(12) United States Patent
Friedrich et al.

(10) Patent No.: US 7,831,295 B2
(45) Date of Patent: Nov. 9, 2010

(54) LOCALIZATION DEVICE CROSS CHECK

(75) Inventors: Dirk Friedrich, Tuttlingen (DE); Nicola Giordano, Villingen-Schenningen (DE); François Leitner, Uriage (FR); Hanns-Peter Tümmler, Tuttlingen (DE)

(73) Assignee: Aesculap AG & Co. KG, Tuttlingen (DE)

( * ) Notice: Subject to any disclaimer, the term of this patent is extended or adjusted under 35 U.S.C. 154(b) by 995 days.

(21) Appl. No.: 10/456,111

(22) Filed: Jun. 5, 2003

(65) Prior Publication Data

US 2004/0249266 A1    Dec. 9, 2004

(51) Int. Cl.
    *A61B 5/05* (2006.01)
(52) U.S. Cl. .................. 600/426; 600/429; 600/410; 600/407; 378/205; 378/206; 378/207; 378/208
(58) Field of Classification Search .......... 600/407, 600/411, 417, 424, 426, 429, 410; 606/30; 378/20, 205
    See application file for complete search history.

(56) References Cited

U.S. PATENT DOCUMENTS

| 2,990,765 | A |   | 7/1961  | Winzenburg |         |
|-----------|---|---|---------|------------|---------|
| 4,963,903 | A |   | 10/1990 | Cane       |         |
| 5,299,288 | A |   | 3/1994  | Glassman et al. |   |
| 5,769,861 | A |   | 6/1998  | Vilsmeier  |         |
| 5,873,822 | A | * | 2/1999  | Ferre et al. | 600/407 |
| 5,971,997 | A | * | 10/1999 | Guthrie et al. | 606/130 |
| 6,122,541 | A |   | 9/2000  | Cosman et al. |      |
| 6,184,922 | B1 |  | 2/2001  | Saito et al. |       |
| 6,385,475 | B1 |  | 5/2002  | Cinquin et al. | 600/407 |
| 6,514,259 | B2 |  | 2/2003  | Picard et al. |      |
| 6,827,733 | B2 |  | 12/2004 | Boneau     |         |
| 6,877,239 | B2 |  | 4/2005  | Leitner et al. |     |
| 6,920,347 | B2 | * | 7/2005  | Simon et al. | 600/424 |
| 2002/0035321 | A1 | * | 3/2002 | Bucholz et al. | 600/407 |
| 2002/0087171 | A1 |   | 7/2002 | Kanesaka |             |
| 2002/0183610 | A1 | * | 12/2002 | Foley et al. | 600/407 |
| 2004/0030245 | A1 |   | 2/2004 | Noble    |              |
| 2004/0054489 | A1 | * | 3/2004 | Moctezuma De La Barrera et al. | 702/105 |
| 2004/0106926 | A1 |   | 6/2004 | Leitner  |              |

FOREIGN PATENT DOCUMENTS

| DE | 19639615      | 4/1998 |
| DE | 10105822      | 8/2002 |
| DE | 203 04 153 U 1 | 5/2003 |
| EP | 1 033 113 A1  | 9/2000 |
| FR | 2 828 801     | 2/2003 |
| JP | 362047513 A   | 3/1987 |
| WO | WO-99/38449   | 8/1999 |

* cited by examiner

*Primary Examiner*—Brian Casler
*Assistant Examiner*—Joel M Lamprecht
(74) *Attorney, Agent, or Firm*—RatnerPrestia (57) ABSTRACT

A method and apparatus for cross checking points palpated with a localization device. Points corresponding to the palpated points are obtained from a preoperative image of an object such as an X-Ray of a tibia bone. During a surgical procedure, the accuracy of palpated points are determined based on the palpated points and corresponding points obtained from the preoperative image. If a palpated point is inaccurate, an indicator is generated to indicate the inaccuracy of the palpated point.

15 Claims, 6 Drawing Sheets

LOCALIZATION DEVICE CROSS CHECK

FIELD OF THE INVENTION

The present invention relates to medical instruments and, more particularly, to a method for cross checking points palpated using a localization device.

BACKGROUND OF THE INVENTION

Localization devices have been developed to assist surgeons in performing surgical procedures. When utilized in a procedure, markers that can be tracked by a stereoscopic camera system are attached to bones. The stereoscopic camera system is connected to a data processing system that records the positions of the markers in space to establish a coordinate reference system relative to each bone bearing a marker. Additional markers may be attached to surgical tools and the localization device programmed with the location of the working portion of the surgical tool relative to the marker. The tool may then be used to palpate (touch) specific landmarks on the bones while the localization device records their location in order to ascertain the position of the landmarks in the coordinate reference systems of the bones. A monitor is used to display information developed from the coordinate reference system and the landmarks for use in guiding a surgeon during the procedure, such as navigating another surgical tool to a particular location in the coordinate reference system.

Typically, the surgical tool used to palpate points on a bone is a pointer. The marker can be mounted on the pointer in only one predetermined way. As noted, the localization device is programmed with data indicating the position of the working portion, e.g., the tip, of the pointer relative to the marker. By observing the marker, the localization device can determine the pointer tip position.

The accuracy of the pointer tip position as determined by the localization device is dependent on several factors. These factors include proper mounting of the marker on the pointer, accurate programming of the data indicating the position of the pointer tip relative to the marker, and trueness of the marker and the pointer. If any of these factors are amiss, the pointer tip position as determined by the localization device will be inaccurate, which, in turn, will result in the development of erroneous information that may be used to guide a surgeon during a surgical procedure. If the information used to guide the surgeon is erroneous, the surgical procedure may be affected adversely. Thus, there is a need to verify the accuracy of points palpated using the localization device to prevent the development of erroneous information based on the palpated points. The present invention fulfills this need among others.

SUMMARY OF THE INVENTION

The present invention provides a method and apparatus to verify the accuracy of points palpated using a localization device. The aforementioned need is satisfied by obtaining points from a preoperative image of an object to be palpated and, during a surgical procedure, determining the accuracy of palpated points based on the palpated points and corresponding points obtained from the preoperative image. If a palpated point is inaccurate, an indicator is generated to indicate the inaccuracy of the palpated point. Verifying the accuracy of palpated points increases the integrity of information developed from the palpated points for guiding a surgeon during a surgical procedure by allowing for corrective actions to be taken during the procedure if an inaccurate palpated point is identified.

One aspect of the present invention is a method for cross checking data points obtained with a localization device during a surgical procedure. The method includes palpating at least two points on an object during the surgical procedure using a surgical tool tracked by the localization device, determining the accuracy of one of the at least two palpated points based on the at least two palpated points and corresponding points obtained from a preoperative image of the object, and generating an indicator if one of the at least two palpated points is inaccurate.

Another aspect of the invention is an apparatus capable of cross checking palpated points acquired with a localization device. The apparatus includes sensors for sensing a surgical tool having a marker, the surgical tool for palpating an object to acquire at least two palpated points; a memory having stored therein data points obtained from a preoperative image of the object, the data points obtained from the preoperative image corresponding to the at least two palpated points; and a computer coupled to the sensors and the memory, the computer configured to determine the accuracy of one of the at least two palpated points based on the at least two palpated points and corresponding points obtained from a preoperative image of the object, the computer generating an indicator if one of the at least two palpated points is inaccurate.

The steps of the method may be embodied in software in a computer readable medium or may form a system comprising means for performing the method steps.

BRIEF DESCRIPTION OF THE DRAWINGS

In the drawings, the same reference numerals are used to indicate the same elements.

DETAILED DESCRIPTION OF THE INVENTION

Figure 1:
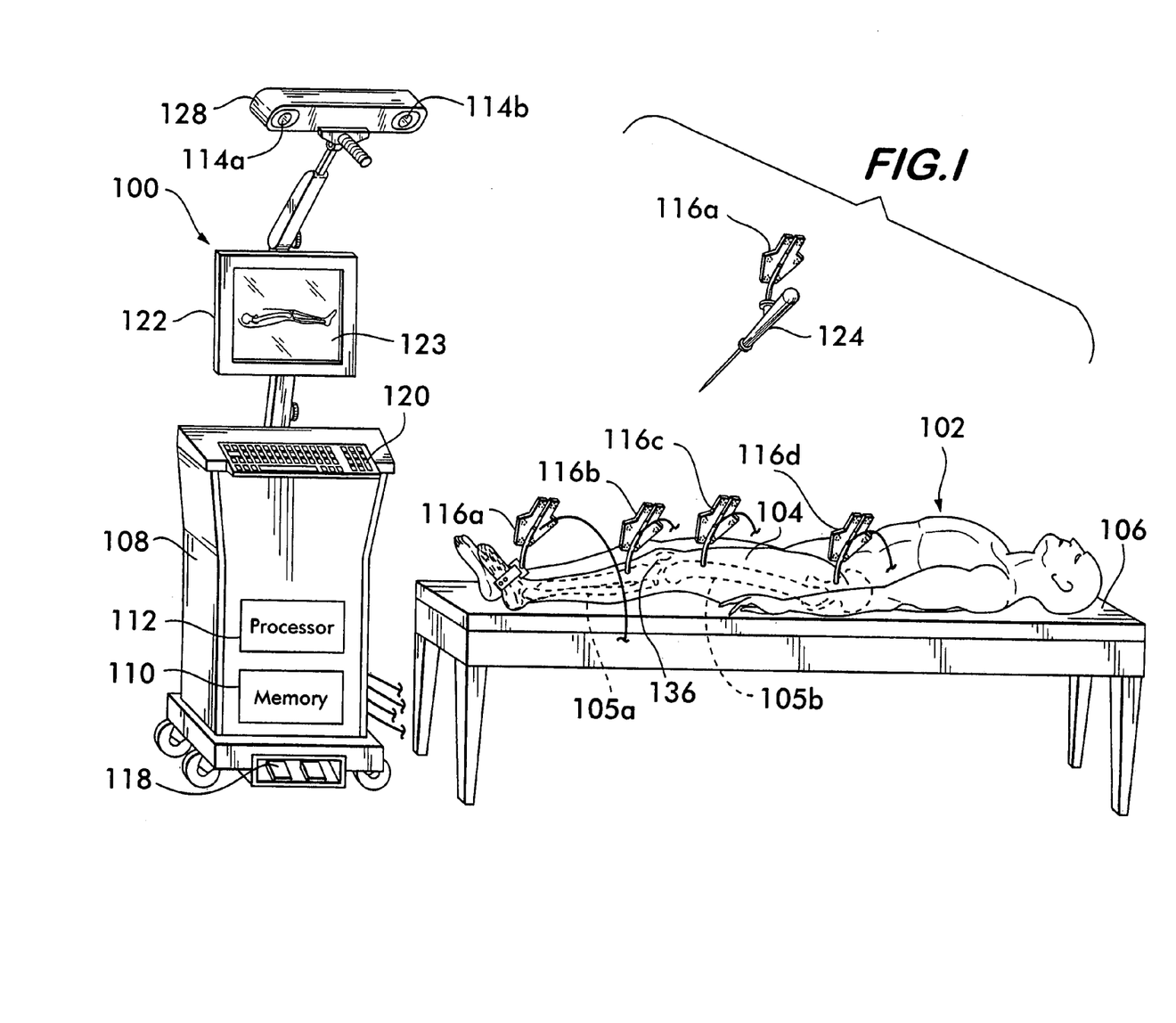
FIG. 1 is an illustration of a patient about to undergo a procedure utilizing a localization device in accordance with the present invention.

FIG. 1 depicts a localization device 100 in which the method of the present invention may be employed. In FIG. 1, a patient 102 who is to undergo a surgical procedure on a leg 104, e.g., a Total Knee Arthroplasty (TKA), is illustrated schematically lying on an operating table 106. The localization device 100 includes a computer 108 loaded with software for surgical navigation, a memory 110, a processor 112, sensors (or cameras) 114 capable of detecting markers 116, a foot pedal 118, a keyboard 120, and a monitor 122 with a display screen 123 for displaying surgical navigation information. The display screen 123 is available to a surgeon for guiding the surgeon during surgical procedures performed using the localization device 100. The sensors 114 are positioned above and laterally from the patient 102 so that the patient's leg 104 is in the field of view of the sensors 114. In general, the markers 116 are fixedly mounted on bones (e.g., a tibia 105a and a femur 105b) and surgical tools (e.g., a pointer 124), so that the localization device 100 can track the exact location and orientation of the bones and surgical tools to which the markers 116 are mounted. A description of a suitable localization device 100 having these features is found in U.S. Pat. No. 6,385,475 to Cinquin et al., having a common inventor and commonly assigned to the same entity as the present application, incorporated fully herein by reference.

Figure 2A:
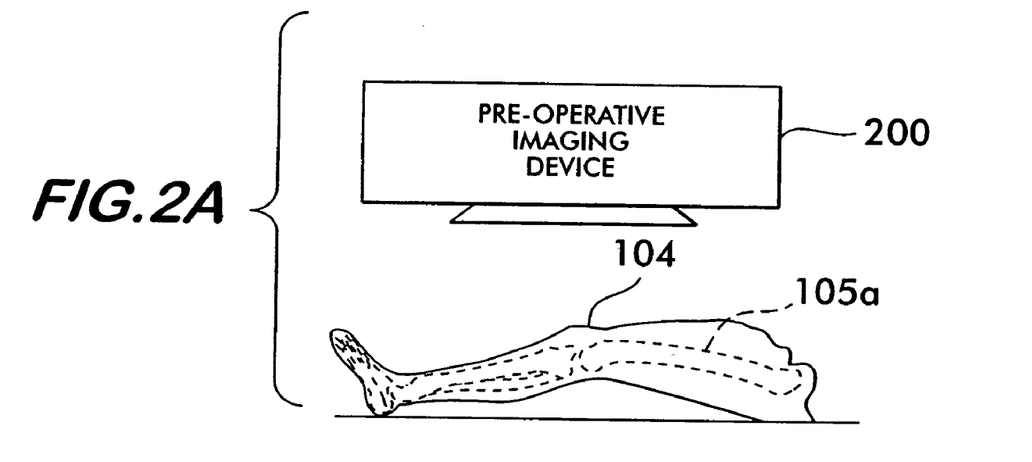
FIG. 2A is an illustration of an imaging device for producing a preoperative image to obtain points corresponding to points obtained using the localization device of FIG. 1.
Figure 2B:
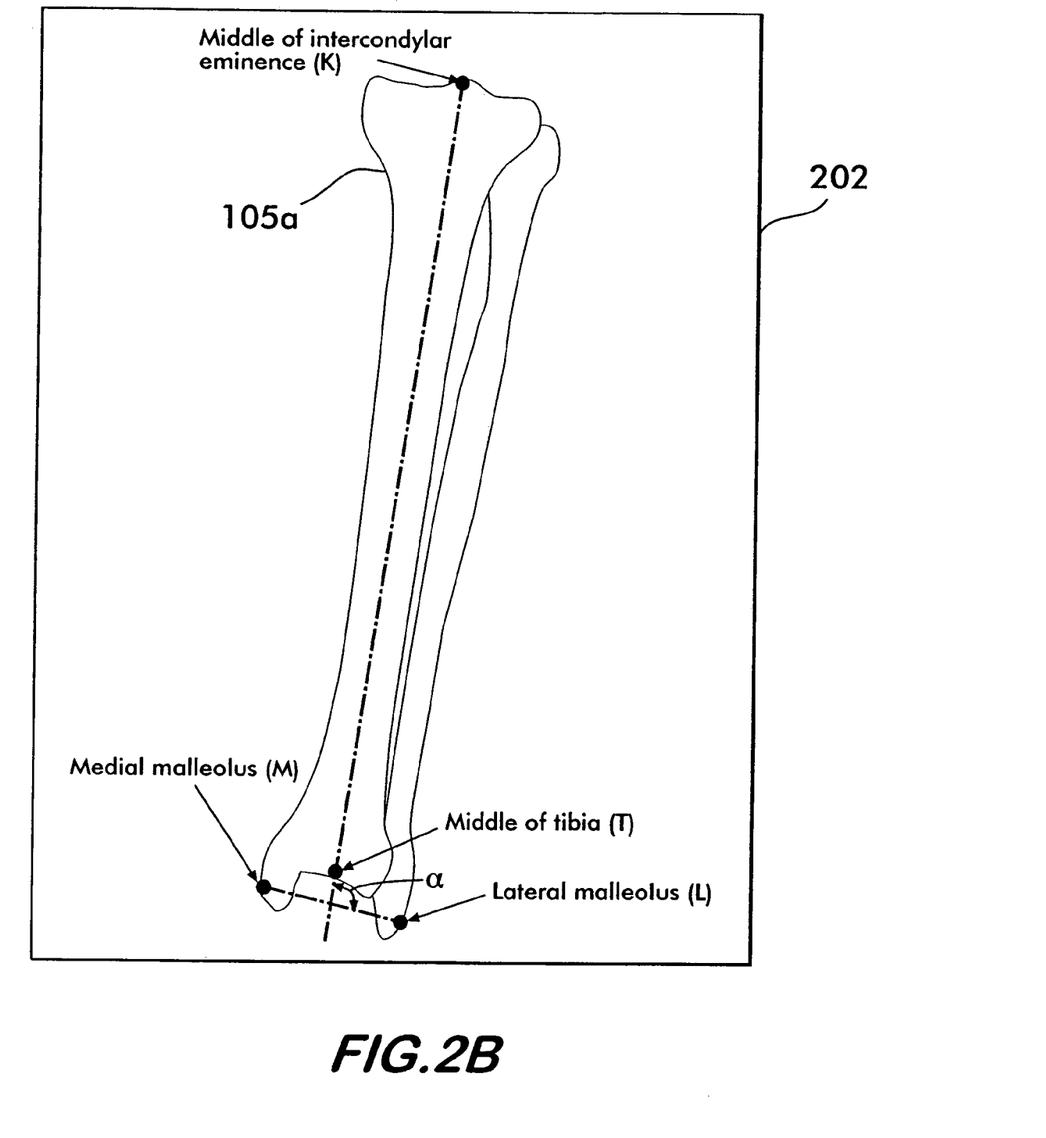
FIG. 2B is an illustration of a preoperative image produced by the imaging device of FIG. 2A.

FIG. 2A depicts a preoperative imaging device 200 for producing a preoperative image of an object, e.g., the tibia 105a within the leg 104, and FIG. 2B depicts an illustrative preoperative image 202 of the tibia 105a produced by such a preoperative imaging device 200. The preoperative image 202 is used to obtain points (i.e., preoperative image points) and features based on the preoperative image points, such as the distance between two points, that can be used to verify the accuracy of palpated points. As will be described in detail below with reference to FIG. 4 and FIG. 5, the accuracy of a point palpated with the localization device 100 (FIG. 1) can be determined based on one or more other palpated points and corresponding preoperative image points. The preoperative imaging device 200 may include a conventional X-Ray, CT-scan, or MRI device, or essentially any device capable of acquiring a preoperative image of an object, e.g., a bone within an appendage. The illustrated preoperative image 202 is a two dimensional image (e.g., a conventional X-Ray image obtained with a conventional X-Ray device or a two dimensional print out of an image obtained with an MRI or CT-scan device). In an alternative embodiment, the preoperative image may be a three dimensional image (e.g., an electronic image obtained with an MRI or CT-scan device). Other imaging devices used for producing preoperative images will be readily apparent to those skilled in the art.

In the illustrated preoperative image 202, the points obtained are the medial malleolus (M), the lateral malleolus (L), the middle of the intercondylar eminence (K), and the middle of the tibia (T) on the ankle extremity. Preferably, the features associated with the preoperative image 202 include measurements such as the distance between two points or the angle between two lines defined by three or more points. For example, the features associated with the preoperative image points may include by way of non-limiting example, the distance between M and L, the distance between K and T, and an angle α between a first line defined by L and M and a second line defined by K and T.

If the preoperative image 202 is a two dimensional "hard" copy, the features can be determined by hand in a known manner, e.g., by marking points directly on the preoperative image 202 and measuring distances between the marked points with a ruler and measuring angles between lines defined by the marked points with a protractor. If the preoperative image 202 is a two dimensional or three dimensional electronic image of the object, the features can be determined using known computer interface technologies, e.g., positioning a cursor on a first point with a conventional computer mouse and selecting that point by depressing a button on the computer mouse and, then, positioning the cursor on a second point and selecting that point. The distance between the two selected points may then be determined automatically in a known manner through the use of known software. Various alternative embodiments for identifying points and features associated with those points will be readily apparent to those skilled in the art.

The obtained points and/or features are stored for later comparison to points palpated using the localization device 100 (FIG. 1) to verify the accuracy of the palpated points. Preferably, the obtained points and/or features are stored in the memory 110 of the localization device 100. In one embodiment, the features are input directly into the localization device 100, e.g. via the keyboard 120, for storage in the memory 110. For example, the localization device 100 may display a prompt on the monitor 122 requesting that the distance between M and L as obtained from the preoperative image 202 be entered into the localization device. An operator, e.g., a surgeon or an assistant, then enters the information into the localization device 100 using the keyboard 120.

In an alternative embodiment, coordinates for the preoperative image points (i.e., data points) are entered directly into the localization device 100. For example, the localization device may prompt the operator to enter the coordinates of the medial malleolus (M) and the lateral malleolus (L), which the operator enters via the keyboard 120, and the localization device will determine the features, e.g., the distance between M and L as needed. In an alternative embodiment, it is contemplated that the data points and/or features are transferred to the localization device 100 directly from an electronic imaging device such as an MRI or CT-scan device. Various alternative embodiments for obtaining and storing data points and/or features associated with the points will be readily apparent to those skilled in the art and those embodiments are considered within the scope of the present invention.

Figure 3:
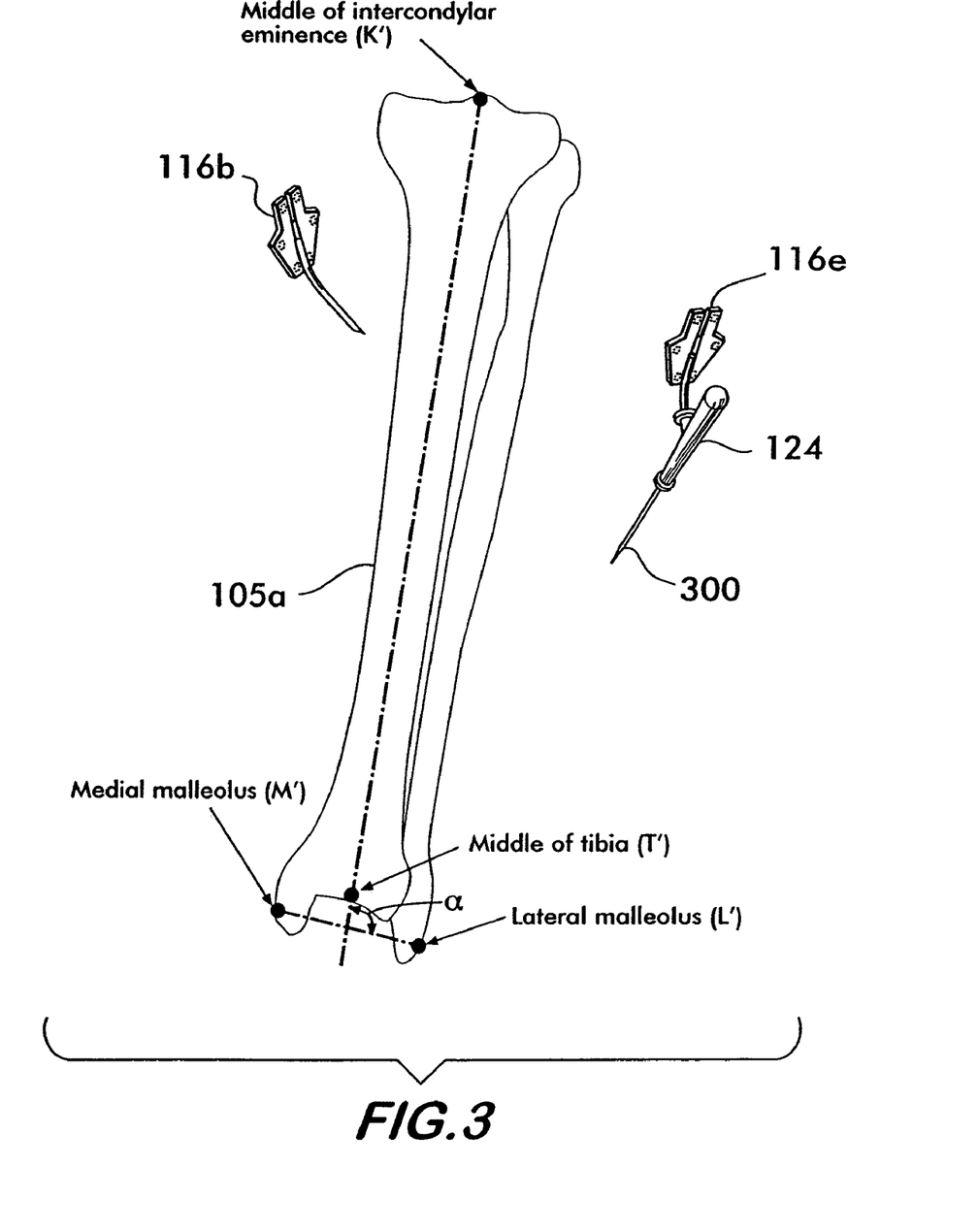
FIG. 3 is an illustration of a tibia to be palpated using the localization device of FIG. 1.

FIG. 3 depicts an object, e.g., the tibia 105a, to be palpated with a surgical tool during a surgical procedure performed using the localization device 100 (FIG. 1). The object is palpated to obtain palpated points and features associated with those points for comparison to corresponding points and features associated with the preoperative image 202 (FIG. 2B). In the illustrated embodiment, the surgical tool is a pointer 124. The pointer 124 has a marker 116e mounted thereon for tracking by the localization device 100. The localization device 100 is preprogrammed with data that indicates the position of the working portion of the pointer 124, i.e., the tip 300, relative to the marker 116e mounted on the pointer 124. During the surgical procedure, the localization device 100 observes the marker 116e on the pointer 124 and determines the position of the pointer tip 300 relative to the tibia 105a, which also has a marker 116b mounted thereon. In a preferred embodiment, the object is palpated by touching the pointer tip 300 to a desired position on the object, e.g., the medial malleolus (M'), and recording the position of the pointer tip in a conventional manner that is well known to those of skill in the art.

The palpated points include by way of non-limiting example, a palpated medial malleolus (M'), a palpated lateral malleolus (L'), a palpated middle of intercondylar eminence (K'), and a palpated middle of tibia (T') on the ankle extremity. Preferably, the palpated points correspond to known points on the preoperative image such as those described above with reference to FIG. 2B. In addition, the localization device 100 determines features associated with the palpated points for comparison to corresponding features associated with points obtained from the preoperative image 202. Preferably, the features associated with the palpated points include measurements such as the distance between two points or the angle between two lines defined by three or more points. For example, the features associated with the preoperative image points may include by way of non-limiting example, the distance between M' and L', the distance between K' and T', and an angle α' between a first line defined by L' and M' and a second line defined by K' and T'. Preferably, the palpated features correspond to features obtained from the preoperative image 202 (FIG. 2B).

Figure 4:
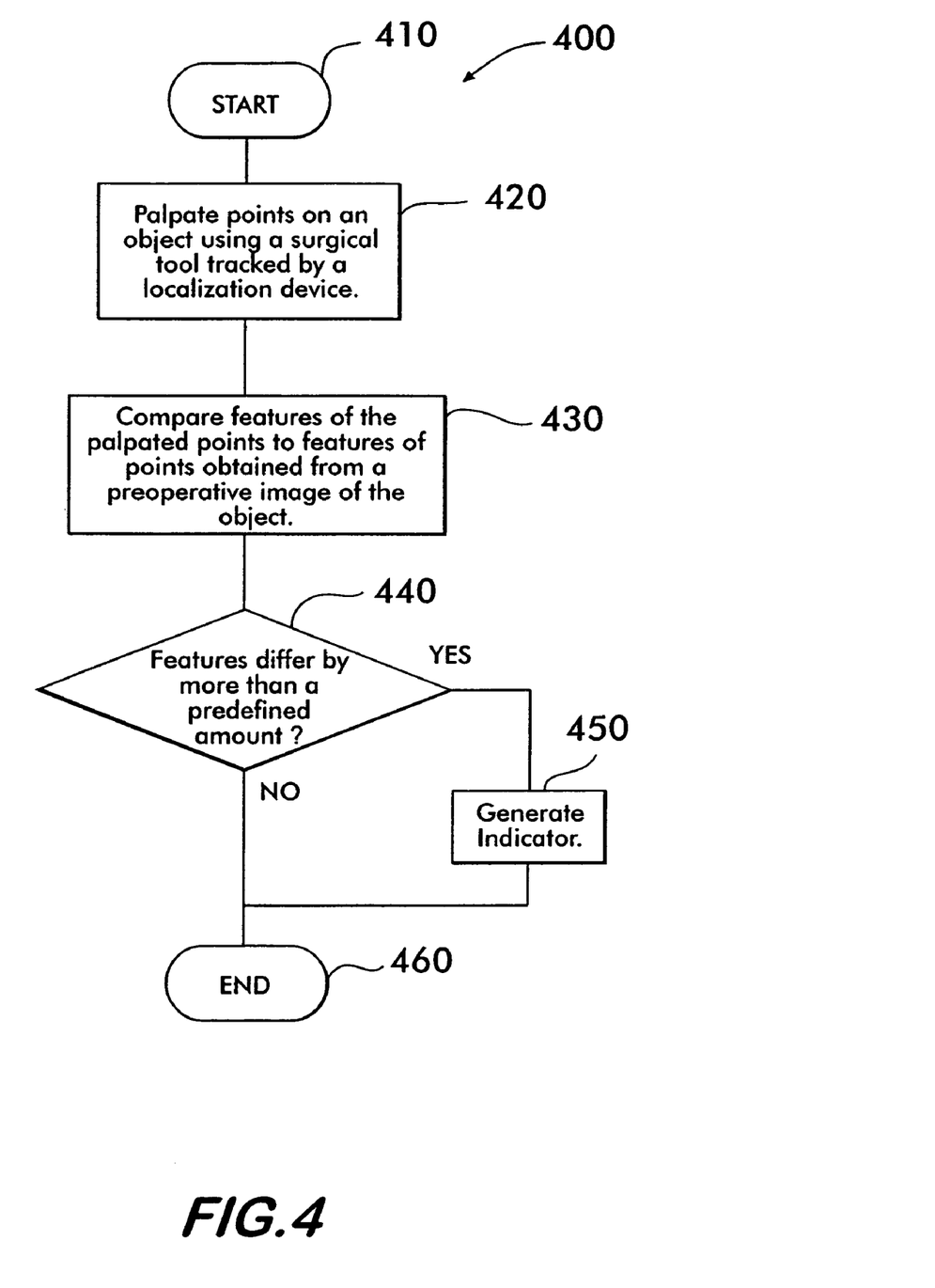
FIG. 4 is a flow chart depicting steps for cross checking points palpated using the localization device of FIG. 1 in accordance with the present invention.

FIG. 4 depicts a flow chart 400 for use in describing a method for cross checking points palpated using the localization device 100 (FIG. 1) in accordance with one embodiment of the present invention. At block 410, the method begins. In a preferred embodiment, the method begins when invoked by the localization device 100 during one or more specific portions of a surgical procedure. For example, the localization device 100 may invoke the method during specific steps of a surgical procedure, e.g., whenever the surgical procedure requires that a point be palpated. In an alternative embodiment, the localization device 100 may invoke the method at the start of the surgical procedure and the method may be used to verify palpated points as needed throughout the entire surgical procedure.

At block 420, an object is palpated using a surgical tool, e.g., pointer 124 (FIG. 1), that is tracked by the localization device 100. In a preferred embodiment, the localization device 100 via the monitor 122 prompts the surgeon to palpate points on the object. For example, the localization device 100 may prompt the surgeon to palpate the following points on the tibia 105a: the medial malleolus (M'), the lateral malleolus (L'), the middle of the intercondylar eminence (K'), and the middle of the tibia (T') at the ankle extremity. Preferably, coordinates of the palpated points and/or features associated with the palpated points are stored in a memory 110 associated with the localization device 100.

At blocks 430 and 440, the accuracy of at least one palpated point is determined. In the embodiment depicted in FIG. 4, features associated with the points palpated at block 420 are compared to features associated with points obtained from a preoperative image 202 (FIG. 2B) of the object to determine if the compared features differ by more than a predefined amount (i.e., a threshold value). The features may include a distances between two points and/or angles defined by three or more points. The threshold value for a distance feature may be a predefined distance, e.g., 10 millimeters, or a predefined percentage, e.g., 2%. The threshold value for an angle may be a predefined angle, e.g., 2°, or a predefined percentage, e.g., 5%. It will be recognized by those skilled in the art that the distances may be scaled in a known manner prior to comparison to compensate for scale differences between palpated points obtained from the actual object and between corresponding points obtained from the preoperative image. In addition, known scaling techniques may be employed to compensate for apparent distance discrepancies attributed to representing a three dimensional object in two dimensions, if applicable. If the compared features exceed the predefined amount, processing proceeds to block 450. Otherwise, processing ends at block 460. Preferably, the features are compared by the localization device 100.

If the feature is a distance between two palpated points, such as the distance between the palpated medial malleolus (M') and the palpated lateral malleolus (L'), the distance can be compared in the following manner. First, the localization device computes the distance between the palpated medial malleolus (M') and the palpated lateral malleolus (L') in a known manner. Then, the localization device compares the computed distance to a measured distance between the medial malleolus (M) and the lateral malleolus (L) in a preoperative image (scaling the computed distance if necessary). The distance between the preoperative image points may be stored in the memory 110 of the localization device for direct comparison to the computed distance or the distance between the preoperative image points may be computed from the coordinates of preoperative image points stored in the memory 110.

If the feature is an angle between three or more palpated points, such as the angle α' between a first line defined by a first vector extending between the palpated medial malleolus (M') and the palpated lateral malleolus (L') and a second line defined by a second vector extending between the palpated middle of the tibia (T') on the ankle extremity and the palpated middle of the intercondylar eminence (K'), the angle feature can be compared in the following manner. First, the localization device computes the angle α' between a first vector extending between the palpated medial malleolus (M') and the palpated lateral malleolus (L') and a second vector extending between the palpated middle of the tibia (T') on the ankle extremity and the palpated middle of intercondylar eminence (K'). Then, the localization device compares the computed angle α' to a measured angle α between a first vector extending between the medial malleolus (M) and the lateral malleolus (L) in a preoperative image and a second vector extending between the middle of the tibia (T) on the ankle extremity and the middle of intercondylar eminence (K') in the preoperative image. The angle α between the preoperative image points may be stored in the memory 110 for direct comparison to the computed angle α'. Alternatively, the angle α defined by the preoperative image points may be computed from the coordinates of preoperative image points stored in the memory 110.

In a preferred embodiment, a feature is compared as the points necessary to define that feature are acquired through palpation. In this manner, it is possible to identify an inaccurate palpated point when it is palpated (or shortly thereafter), thus maximizing the amount of time available to remedy the inaccuracy. For example, if the feature is a distance between two points, the feature for the palpated points will be compared to the corresponding feature obtained from points on a preoperative image immediately after acquiring the second of the two palpated points. At this time, if the palpated feature and the preoperative image feature differ by more than the threshold value for that feature, processing will proceed to block 450.

At block 450, an indicator is generated that indicates that the threshold value of a feature compared in blocks 430 and 440 has been exceeded. The indicator may be a visual indicator displayed on the monitor 122 of the localization device 100 and/or an audible indicator emitted from an audio device (not shown) associated with the localization device 100. In a preferred embodiment, the presence of an indicator alerts a surgeon during the palpation of points to the possibility of a palpated point that is inaccurate, which may result in the development of erroneous information by the localization device 100. Alerting the surgeon during the palpation of the points allows the surgeon to take corrective action during the procedure. For example, the surgeon may palpate one or more of the points again, replace the surgical tool, and/or replace the marker mounted on the surgical tool.

Thus, the method can be used to cross check points palpated on an object using a localization device by comparing features associated with the palpated points to corresponding features associated with points obtained from a preoperative image of the object in the following manner. The localization device 100 of FIG. 1 invokes the method of FIG. 4 during a step of a surgical procedure in which points are to be palpated using the localization device 100. After at least two points are palpated, a feature associated with these palpated points, e.g., the distance between two of the palpated points, can be determined for comparison to a corresponding feature associated with a preoperative image, e.g., the distance between two points on the preoperative image that correspond to the two palpated points. If the difference between a feature associated with the palpated points and a corresponding feature associated with the preoperative image points differs by more than a predetermined amount, an indicator is generated to indicate that one of the palpated points on which the feature is based may be erroneous. Corrective action may then be taken in response to the identification of an erroneous palpated point to increase the integrity of information generated by the localization device from the palpated points for use in guiding a surgeon during a surgical procedure.

Figure 5:
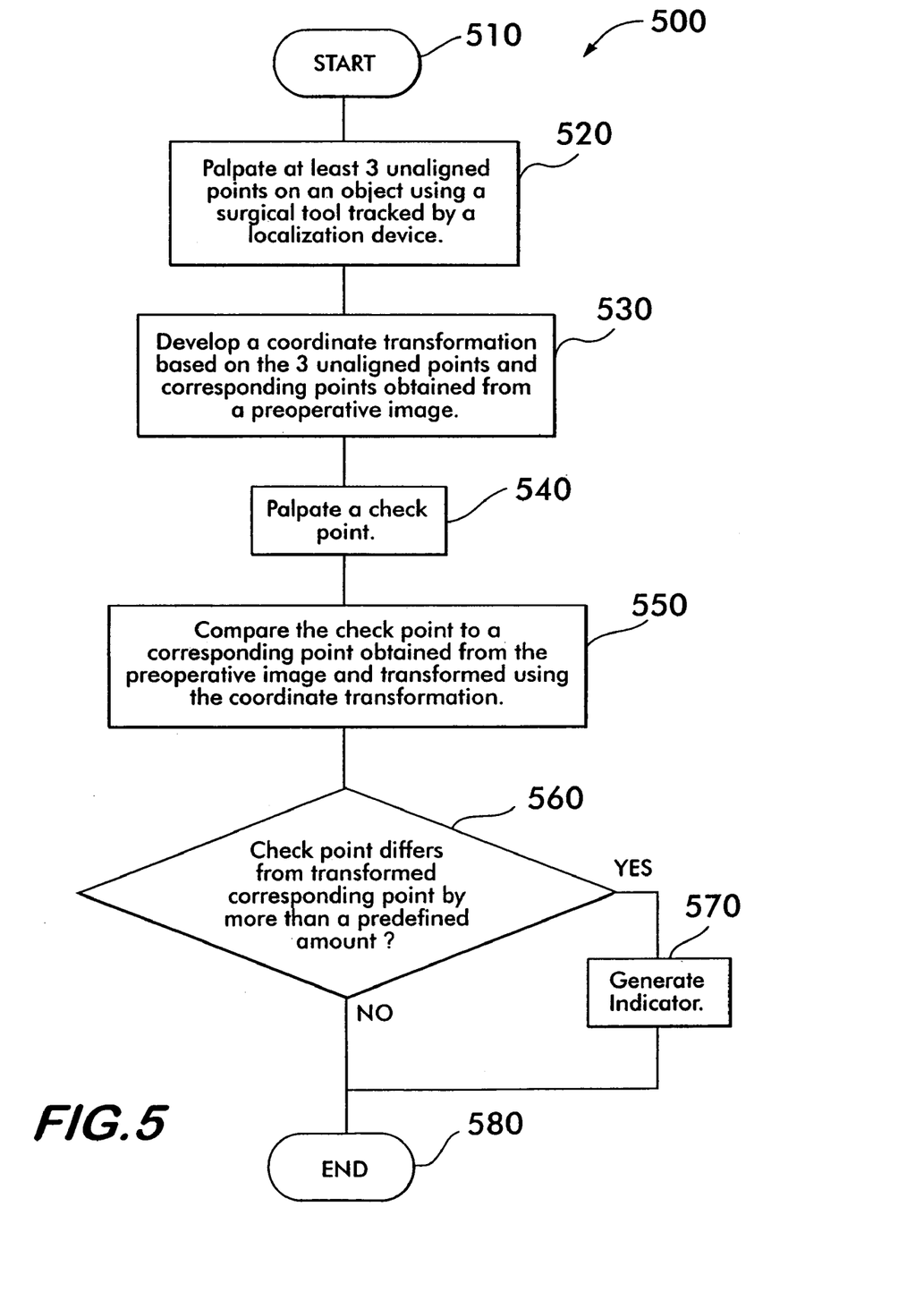
FIG. 5 is a flow chart depicting alternative steps for cross checking points palpated using the localization device of FIG. 1 in accordance with the present invention.

FIG. 5 depicts a flow chart 500 for use in describing an alternative method for cross checking points palpated using the localization device 100 (FIG. 1). At block 510, the method begins as described above in reference to block 410 (FIG. 4). At block 520, an object is palpated using a surgical tool, e.g., pointer 124 (FIG. 1), that is tracked by the localization device 100 to acquire at least three unaligned points. In a preferred embodiment, the localization device 100 via a monitor 122 prompts the surgeon to palpate points on the object. For example, the localization device 100 may prompt the surgeon to palpate the following points on the tibia 105a: the medial malleolus (M'), the lateral malleolus (L'), and the middle of the tibia (T') at the ankle extremity depicted in FIG. 3. Preferably, the coordinates of the palpated points are stored in the memory 110 associated with the localization device 100.

At blocks 530-560, the accuracy of at least one palpated point is determined (i.e., a check point). The check point is a palpated point other than the at least three unaligned points palpated at block 520, e.g., the middle of the intercondylar eminence (K') depicted in FIG. 3. In a preferred embodiment, as will be described in detail below, the accuracy of the check point is determined by developing a coordinate transformation based on the at least three unaligned points palpated at block 520 and corresponding points obtained from a preoperative image. The check point is then compared to a corresponding point obtained from the preoperative image, e.g., the middle of the intercondylar eminence (K) depicted in FIG. 2B. Prior to comparison, the corresponding point is transformed using the coordinate transformation. If the check point differs from the transformed corresponding point by more than a predefined amount, an indication is generated that indicates the palpated check point is erroneous.

At block 530, the coordinate transformation is developed. The coordinate transformation is an algorithm based on the at least three unaligned points palpated at block 520 and corresponding points obtained from the preoperative image, e.g., the medial malleolus (M), the lateral malleolus (L), and the middle of the tibia (T) at the ankle extremity depicted in FIG. 2B. For illustrative purposes, the three unaligned palpated points are represented by the coordinate triplet (Ap,Bp,Cp) with each letter in the triplet corresponding to the coordinates of one of the three unaligned points, and the corresponding points obtained from the preoperative image (i.e., model) are represented by the coordinate triplet (Am,Bm,Cm) with similar capital letters indicating corresponding points.

In a preferred embodiment, the coordinate transformation is generated by, first, identifying points for first and second palpated points, e.g., Ap and Bp, that are within a neighborhood, i.e., within a predefined distance, of the palpated points, respectively. The number of points identified is dependent on the resolution of the system. For example, if the resolution of the system is 1,000 points per square inch and the neighborhood surrounding each palpated point is equivalent to one square inch, 100,000 points will be identified for each palpated point. For palpated points Ap and Bp, the points within the neighborhood of these points are represented by Ai and Bi, respectively, where i is 1 to n, n being the total number of points in a neighborhood. Then, all points in the neighborhood of the first palpated point, e.g., Ai, are identified where a point in Bi exists that is a distance d1 from Ai, where the distance d1 is the distance between corresponding points from the preoperative image, e.g., Am, Bm. These criteria are illustrated in the following equations 1-3:

$$d(Ap, Ai) < \delta \quad (1)$$
(where, $d$ is distance and $\delta$ is neighborhood size)

$$d(Bp, Bi) < \delta \quad (2)$$

$$d(Ai, Bi) = d1(Am, Bm) \quad (3)$$

(Preferably, if no point Ai in the neighborhood of the first palpated point, e.g., Ap, satisfies equations 1-3, an indicator is generated to indicate that the coordinate transformation can not be developed based on the palpated points.)

Next, all points within the neighborhood of a third palpated point, e.g., Cp, are identified. For palpated point Cp, the points within the neighborhood are represented by Ci. Then, using all first and second points, e.g., (Ai,Bi), that satisfy the criteria of equations 1-3 above, all points in the neighborhood of the third palpated point, e.g., Ci, are identified where a point in Ci exists that is a distance d2 from Ai, where d2 is the distance between two corresponding points from the preoperative image, e.g., Am, Cm; and where an angle α between a first vector, e.g., (AiBi), and a second vector, e.g., (AiCi), is the same as an angle from the preoperative image between a third vector, e.g., (AmBm), and a fourth vector, e.g., (AmCm). These criteria are illustrated in the following equations 4-6:

$$d(Cp, Ci) < \delta \quad (4)$$

$$d(Ai, Ci) = d2(Am, Cm) \quad (5)$$

$$\alpha(AiBi, AiCi) = \alpha(AmBm, AmCm) \quad (6)$$

(Preferably, if no set of points (Ai,Bi) exists that satisfies equations 1-6, an indicator is generated to indicate that the coordinate transformation can not be developed based on the palpated points.)

Then, for all sets of points, e.g., (Ai,Bi,Ci), that satisfy equations 1-6, a transformation triplet (Ao,Bo,Co) is identified wherein the sum of the distances between each point of the transformation triplet and a corresponding palpated point is minimum. This criteria is illustrated in the following equation 7:

$$\text{Minimum} \Sigma_i d(Ai, Ap) + d(Bi, Bp) + d(Ci, Cp) \quad (7)$$

The transformation triplet (Ao,Bo,Co) satisfies equations 1-7 and is used to generate the coordinate transformation. The generation of the coordinate transformation from the triplet (Ao,Bo,Co) will be readily apparent to those of skill in the art.

At block 540, a check point, Dp, is palpated. As noted above, the palpated check point is a point other than the three unaligned points palpated at block 520, e.g., the middle of the intercondylar eminence (K'). The check point is palpated as described above with reference to block 520. Preferably, the coordinates of the palpated point are stored in the memory 110 associated with the localization device 100.

At blocks 550 and 560, the check point palpated at block 540 is compared to a corresponding point, Dm, from the preoperative image, e.g., the middle of the intercondylar eminence (K). Prior to comparison, the corresponding point from the preoperative image is transformed using the coordinate transformation developed at block 530. Using the coordinate transformation developed at block 520, the coordinates of the corresponding point Dm are transformed in a known manner to obtain a transformed point Do. The check point Dp is then compared to the transformed point Do to see if the check point Dp is within the neighborhood of the transformed point Do. Specifically, the points are compared to determine if the check point differs from the transformed point Do by more than a predefined amount, e.g., 10 millimeters or 2%. The criteria for determining if the transformed point differs from the transformed corresponding point is illustrated in the following equation 8:

$$d(Dp,Do)<\delta \qquad (8)$$

If the check point differs from the transformed image point, processing proceeds to block 570—where an indicator is generated as described above with reference to block 450. Otherwise, processing ends at block 580.

Thus, as with the method described above with reference to FIG. 4, the alternative method described with reference to FIG. 5 can be used to cross check points palpated on an object using a localization device. The embodiment depicted in FIG. 5 accomplishes cross checking of palpated points in the following manner. The localization device 100 of FIG. 1 invokes the method of FIG. 5 during a step of a surgical procedure in which points are to be palpated using the localization device 100. After at least three points are palpated, a coordinate transformation can be developed based on the palpated points and corresponding points from a preoperative image. The coordinate transformation is then used to transform the coordinates of any point from a preoperative image for comparison to a corresponding palpated point to determine the accuracy of the palpated point. If the difference between the transformed point and the corresponding palpated point exceeds a predetermined amount, an indicator is generated to indicate that the palpated point may be erroneous. Corrective action may then be taken in response to the identification of an erroneous palpated point to increase the integrity of information generated by the localization device from the palpated points for use in guiding a surgeon during a surgical procedure.

The processing steps of the present invention can be implemented by computer programs in conjunction with hardware components. Software programming code which embodies the present invention may be stored on any of a variety of known media such as a diskette, hard drive, or CD-ROM, and may be distributed on such media. The techniques and methods for embodying software programming code on physical media and/or distributing software code are known in the art.

Having thus described a few particular embodiments of the invention, various alterations, modifications, and improvements will readily occur to those skilled in the art. Such alterations, modifications and improvements as are made obvious by this disclosure are intended to be part of this description though not expressly stated herein, and are intended to be within the spirit and scope of the invention. Accordingly, the foregoing description is by way of example only, and not limiting. The invention is limited only as defined in the following claims and equivalents thereto.

What is claimed is:

1. A method for cross checking data points obtained with a localization device during a surgical procedure, said method comprising the steps of:

palpating at least three unaligned points on an object during the surgical procedure using a surgical tool tracked by a localization device, the three unaligned palpated points corresponding to three points obtained from a preoperative image of said object;

determining the accuracy with which said localization device determines a location of one of said at least three unaligned palpated points by developing a coordinate transformation based on said at least three unaligned palpated points and said three corresponding points obtained from said preoperative image; palpating a check point during the surgical procedure using said surgical tool, the palpated check point corresponding to a fourth point obtained from the preoperative image; transforming said fourth corresponding point obtained from the preoperative image using said coordinate transformation; and comparing said palpated check point to said transformed corresponding point to determine if it is accurate; and generating an indicator if said palpated check point is inaccurate, said palpated check point being inaccurate if said palpated check point differs from said transformed corresponding point by more than a predefined amount.

2. The method of claim 1, wherein said determining step further comprises:

comparing a feature associated with said at least three palpated points to a corresponding feature associated with said three corresponding points obtained from said preoperative image of said object.

3. The method of claim 2, wherein said one of said at least three palpated points is determined to be inaccurate if said feature differs from said corresponding feature by more than a predefined amount.

4. The method of claim 2, wherein said comparing step comprises at least the step of:

comparing the distance between two of the at least three palpated points and the distance between corresponding points obtained from said preoperative image.

5. The method of claim 4, wherein said step of comparing the distance comprises at least the step of:

scaling the distance between said corresponding points obtained from said preoperative image to match the scale of the distance between said two of the at least three palpated points.

6. The method of claim 2, wherein said comparing step comprises at least the step of:

comparing a first angle to a second angle, said first angle formed between a first line extending between two of said at least three palpated points and a second line extending between two of said at least three palpated points, at least one point within said first line not being in said second line, said second angle formed between a third line extending between points on said preoperative image corresponding to said two of said at least three palpated points defining said first line and a fourth line extending between points on said preoperative image corresponding to said two of said at least three palpated points defining said second line.

7. The method of claim 1, wherein the surgical tool is a pointer having a marker.

8. The method of claim 1, wherein the object is a bone.

9. The method of claim 1, wherein said preoperative image is produced by a preoperative imaging device selected from a group consisting of an X-Ray device, an MRI device, and a CT-scan device.

10. An apparatus capable of cross checking palpated points acquired with a localization device, said apparatus comprising:

sensors for sensing a surgical tool having a marker, said surgical tool for palpating an object to acquire at least three unaligned palpated points corresponding to three points obtained from a preoperative image of said object and a check point corresponding to a fourth point obtained from said preoperative image of said object;

a memory; and a computer coupled to said sensors and said memory, said computer configured to determine the accuracy with which said localization device determines a location of the check point by developing a coordinate transformation based on said at least three unaligned palpated points and said three corresponding points obtained from said preoperative image, transforming said fourth corresponding point obtained from said preoperative image of said object using said coordinate transformation, and comparing said palpated check point to said transformed corresponding point, wherein said computer generates said indicator if said palpated check point differs from said transformed corresponding point by more than a predefined amount.

11. The apparatus of claim 10, wherein said computer determines the accuracy of said one of said at least three unaligned palpated points by comparing at least one feature associated with said at least three unaligned palpated points to a corresponding feature associated with said three corresponding points obtained from said preoperative image and generates said indicator if said at least one feature differs from said corresponding feature by more than a predefined amount.

12. The method of claim 10, wherein said object is a bone.

13. The method of claim 10, wherein said image is produced by a preoperative imaging device selected from a group consisting of an X-Ray device, an MRI device, and a CT-scan device.

14. A non-transitory computer readable medium including program code for cross checking data points obtained with a localization device during a surgical procedure, the non-transitory computer readable medium comprising:

computer readable program code for palpating at least three unaligned points on an object during the surgical procedure using a surgical tool tracked by the localization device, the three unaligned palpated points corresponding to three points obtained from a preoperative image of said object;

computer readable program code for determining the accuracy with which said localization device determines a location of one of said at least three unaligned palpated points by developing a coordinate transformation based on said at least three unaligned palpated points and said three corresponding points obtained from said preoperative image, palpating a check point during the surgical procedure using said surgical tool, the palpated check point corresponding to a fourth point obtained from the preoperative image, transforming said fourth corresponding point obtained from the preoperative image using said coordinate transformation, and comparing said palpated check point to said transformed corresponding point obtained from the preoperative image to determine if it is accurate; and computer readable program code for generating an indicator if said palpated check point is inaccurate.

15. The product of claim 14, wherein said computer readable program code for determining comprises at least:

computer readable program code for comparing a feature associated with said at least three unaligned palpated points to a corresponding feature associated with said three corresponding points obtained from said preoperative image of said object.

* * * * *